(12) United States Patent
Schiffer et al.

(10) Patent No.: US 6,639,108 B2
(45) Date of Patent: Oct. 28, 2003

(54) AMMOXIMATION OF KETONES AND WORK-UP BY PERVAPORATION/VAPOR PERMEATION

(75) Inventors: Thomas Schiffer, Haltern (DE); Peter Ernst Esser, Aschheim (DE); Martin Roos, Haltern (DE); Franz-Felix Kuppinger, Marl (DE); Günter Stevermüer, Marl (DE); Georg Friedrich Thiele, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/232,371

(22) Filed: Sep. 3, 2002

(65) Prior Publication Data

US 2003/0105356 A1 Jun. 5, 2003

(30) Foreign Application Priority Data

Aug. 31, 2001 (DE) .......................... 101 42 620

(51) Int. Cl.$^7$ ...................... C07C 249/08; C07C 249/14
(52) U.S. Cl. ...................... 564/264; 564/259
(58) Field of Search ................... 564/259, 264

(56) References Cited

U.S. PATENT DOCUMENTS

| | | | |
|---|---|---|---|
| 4,745,221 A | 5/1988 | Roffia et al. | |
| 4,794,198 A | 12/1988 | Roffia et al. | |
| 5,041,652 A | 8/1991 | Padovan et al. | |
| 5,227,525 A | 7/1993 | Tonti et al. | |
| 5,312,987 A | 5/1994 | Mantegazza et al. | |
| 5,451,701 A | 9/1995 | Zajacek et al. | |
| 5,498,793 A | 3/1996 | Mantegazza et al. | |
| 5,599,987 A | 2/1997 | Crocco et al. | |
| 5,637,715 A | 6/1997 | Thiele et al. | |
| 2002/0058840 A1 | 5/2002 | Thiele et al. | |

FOREIGN PATENT DOCUMENTS

| | | |
|---|---|---|
| DE | 195 21 011 | 12/1995 |
| DE | 100 47 435 | 4/2002 |
| DE | 101 03 581 | 8/2002 |
| EP | 0 208 311 | 1/1987 |
| EP | 0 267 362 | 5/1988 |
| EP | 0 299 430 | 1/1989 |
| EP | 0 496 385 | 7/1992 |
| EP | 0 564 040 | 10/1993 |
| EP | 0 690 045 | 1/1996 |
| EP | 0 735 017 | 10/1996 |

OTHER PUBLICATIONS

F. Lipnizki, et al., Journal of Membrane Science, vol. 153, no. 2, pp. 183–210, "Pervaporation–Based Hybrid Process: A Review of Process Design, Applications and Economics", Feb. 17, 1999.

Primary Examiner—Brian Davis
(74) Attorney, Agent, or Firm—Oblon, Spivak, McClelland, Maier & Neustadt, P.C.

(57) ABSTRACT

A process for the work-up of a reaction mixture formed by ammoximation of a ketone, in particular an alkanone or cycloalkanone, by means of hydrogen peroxide and ammonia in homogeneous solution over a titanium-containing catalyst. It comprises the substeps removal of the catalyst, selective separation of the oxime formed in the ammoximation from the reaction mixture, removal of water of reaction and recirculation of the solvent. The work-up is carried out using at least one membrane separation step and is also successful in the case of incomplete ketone conversion and in the presence of dissolved salts.

20 Claims, 2 Drawing Sheets

AMMOXIMATION OF KETONES AND WORK-UP BY PERVAPORATION/VAPOR PERMEATION

BACKGROUND OF THE INVENTION

1. Field of the Invention

The present invention relates to the work-up of a reaction mixture formed by ammoximation of a ketone by means of hydrogen peroxide and ammonia, wherein the work-up process comprises at least one membrane separation step.

2. Background of the Invention

Numerous patent applications and patents describe the ammoximation of ketones, in particular alkanones and/or cycloalkanones, by means of hydrogen peroxide and ammonia over a heterogeneous catalyst system which comprises at least one component composed of the elements titanium, silicon and oxygen.

Examples which may be mentioned here are EP-A-0 299 430, EP-A-0 564 040 and U.S. Pat. No. 5,637,715.

In general, the catalyst used is a microporous or mesoporous titanium zeolite, with the titanium silicalite TS1 being particularly suitable for ammoximation. Furthermore, in the case of bulky ketones such as alkanones or cycloalkanones, it is advantageous to supplement the catalyst system with further components. Thus, DE 195 21 011 describes and claims amorphous silicates, DE 100 47 435 describes and claims acidic solids and DE 101 03 581 describes and claims ammonium ions as cocatalyst.

As described in DE 100 47 435 and DE 101 03 581, the reaction of bulky (cyclo)alkanones such as cyclododecanone proceeds particularly quickly and selectively in polar organic solvents which are completely or partially miscible with water, in particular in short-chain alcohols having from 1 to 6 carbon atoms.

The ammoximation occurs in two substeps comprising hydroxylamine formation (1) and oximation (2). Water is firstly introduced by means of an aqueous hydrogen peroxide solution and, secondly, water is formed in stoichiometric amounts as reaction product in the two substeps.

In addition, water is also formed in the unproductive decomposition of hydrogen peroxide and hydroxylamine, formally shown in the secondary reactions (3) and (4) of the following reaction scheme formulated for cyclododecanone (CDON) as an example:

$$NH_3 + H_2O_2 \rightarrow H_2O + NH_2OH \tag{1}$$

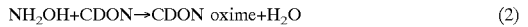
$$NH_2OH + CDON \rightarrow CDON\ oxime + H_2O \tag{2}$$

$$2NH_2OH + H_2O_2 \rightarrow 4H_2O + N_2 \tag{3}$$

$$2H_2O_2 \rightarrow 2H_2O + O_2 \tag{4}$$

Consequently, the water content of the reaction mixture increases during the reaction. If large alkanones or cycloalkanones such as cyclododecanone are to be ammoximated, the solubility of the corresponding oxime in the reaction mixture drops sharply with increasing water content.

A particular objective in the reaction of large cycloalkanones is therefore to restrict the amount of water during the reaction as much as possible. According to DE 100 47 435 and DE 101 03 581, this is achieved, for example, by ammonia being used as dry gas and hydrogen peroxide being used as a very concentrated solution (usually >30% by weight). It is also advantageous for the alcohols used as solvent to contain, at the beginning of the reaction, no more water than is present in the azeotrope after distillation.

If the alcohol is to be used a number of times in the process, the amount of water introduced during the reaction has to be separated off again in the work-up.

In most patent applications, the synthesis of the catalyst system, its activation and the ammoximation reaction itself are the focal points of the investigations. On the subject of the work-up, the abovementioned documents state in general terms that the usually pulverulent catalyst, in general a titanium silicalite, is separated off via a filter or a pressure filter. Conversion and selectivities are subsequently determined by GC analysis and the peroxide consumption is determined directly on the reaction solution by redox titration. If the reaction mixture is worked up further, purification by distillation and/or extraction are chosen for this purpose.

In the European patent applications EP-A-0 690 045 and EP-A-0 735 017, ARCO Chemical Technology describes a multistage process for the synthesis of caprolactam in which the ammoximation of cyclohexanone is carried out using hydrogen peroxide from the reaction of isopropanol and oxygen. For the ammoximation of cyclohexanone, any suitable work-up process is claimed in general terms. EP-A-0 735 017 mentions distillation and extraction as possibilities without these two methods being placed on a concrete basis by means of experimental data or examples.

Complete separation of solvent, starting material and product by distillation after the ammoximation stage, as envisaged in U.S. Pat. No. 5,451,701 and EP-A-0 690 045, might well be possible in the case of cyclohexanone oxime. After the solvent and water have been distilled off, cyclohexanone (b.p. 155° C./1013 mbar) and cyclohexanone oxime (b.p. 206–210° C./1013 mbar) can be separated from one another by distillation. This distillation is advantageously carried out under reduced pressure.

However, a method involving purely distillation is no longer suitable for the ammoximation of macrocyclic ketones such as cyclododecanone. The separation of ketone and oxime by distillation becomes increasingly difficult as the ring size increases, and, in addition, the high distillation temperatures even in a high vacuum result in a considerable degree of decomposition. Cyclododecanone oxime, for example, can no longer be distilled without decomposition.

A number of publications mention extraction for the work-up. In EP-A-0 208 311, example 1, Montedipe describes the reaction of cyclohexanone and work-up of the ammoximation product of cyclohexanone without alcohol as solvent in a three-phase mixture (organic-aqueous-solid) comprising cyclohexanone as organic phase, 32% strength by weight aqueous ammonia and 32% strength by weight aqueous hydrogen peroxide as aqueous phase and pulverulent titanium silicalite as solid catalyst. For the work-up and removal of the catalyst, the organic phase is taken up in toluene, the aqueous phase is extracted a number of times with toluene and the catalyst is separated off by filtration.

In the patent U.S. Pat. No. 4,794,198 and the European patent application EP-A-0 267 362, an organic solvent, for example an ether, is added to the cooled reaction mixture after the ammoximation and the cyclohexanone and the corresponding oxime are extracted by means of this.

According to EP-A-0 496 385, Enichem firstly distills off an ammonia-containing azeotrope of solvent, tert-butanol and water. The oxime and alkanone are subsequently washed out of the distillation bottoms by means of toluene in an extractor.

The above-mentioned work-up processes have, in particular, two disadvantages:

The ketone used in each case and its corresponding oxime firstly become increasingly similar in terms of their extraction behavior as the size of the molecule increases and although they can be removed from the reaction mixture together with the extractant used, they can be separated from one another only incompletely, if at all. A ketone-free oxime can be obtained in this way only in the case of complete conversion of the ketone.

However, it is known from numerous documents, for example DE 100 47 435 and DE 101 03 581, that the reactivity of ketones in the ammoximation reaction decreases with increasing size. Complete conversions of bulky ketones are only possible at long reaction times and with a high peroxide consumption (=poor peroxide selectivity).

A further disadvantage of the abovementioned work-up methods is that the distillation of the solvent mixture requires a large amount of energy.

Since low-boiling, short-chain alcohols having preferably from 1 to 6 carbon atoms are preferably used in ammoximation processes for large alkanones and cycloalkanones, the removal of the water of reaction by rectification or distillation results in the total amount of alcoholic solvent going over at the top of one or more columns. This means that the enthalpy of vaporization for the total amount of solvent has to be introduced. In the subsequent condensation of the solvent, this energy has to be passed to a cooling medium. Despite the use of heat exchangers, these processes have a considerable energy consumption which has a very adverse effect on the economics of these processes.

In addition, the above-described solvent distillation is unsuitable in the case of incomplete ketone conversions and/or in the case of incomplete separation of the oxime from the reaction mixture, since these compounds accumulate in the stripping section or the bottom of the column and can crystallize out there.

SUMMARY OF THE INVENTION

It is therefore an object of the invention to find an energy-saving work-up process for the ammoximation of ketones, in particular bulky alkanones and cycloalkanones having, in particular, from 8 to 20 carbon atoms, in which the catalyst is separated off after the reaction, the oxime is isolated selectively from the reaction mixture, the water of reaction is separated off from the solvent in an energy-saving manner and the solvent which remains is returned to the process, and which can be carried out even in the case of incomplete conversion in the ammoximation.

It has surprisingly been found that the solubility of ketone oximes, in particular many alkanone oximes and cycloalkanone oximes in short-chain alcohols is highly temperature dependent. The oximes can thus be separated very selectively from the reaction mixture even at incomplete ketone conversion by means of suitable temperature conditions. Even a single-stage crystallization achieves oxime purities of above 99% by weight, which are sufficient for direct further use of the oximes without additional purification steps, for example in a Beckmann rearrangement.

In addition, it has surprisingly been found that water can be removed very selectively and in an energy-saving manner from the remaining mother liquor by preparation or vapor permeation through membranes and that this work-up step is also possible in the case of incomplete ketone conversion and the resulting presence of ketones.

The invention accordingly provides a process for the work-up of a reaction mixture formed by ammoximation of a ketone, in particular an alkanone or cycloalkanone having, in particular, from 8 to 20 carbon atoms, by means of hydrogen peroxide and ammonia in homogeneous solution over a titanium-containing catalyst, which comprises the substeps removal of the catalyst, selective separation of the oxime formed in the ammoximation from the reaction mixture, removal of water of reaction and recirculation of the solvent, wherein the work-up process is carried out, even in the case of incomplete ketone conversion, by use of at least one membrane separation step.

Accordingly, the present invention is directed to a process for the work-up of a reaction mixture containing an oxime formed by ammoximation of a ketone with hydrogen peroxide and ammonia in a homogeneous solution containing a solvent over a titanium-containing catalyst, comprising the steps of:

removing the catalyst, separating the oxime from the reaction mixture, removing water of reaction from the reaction mixture, and recirculating the solvent, wherein at least one of said steps comprises a membrane separation.

A more complete appreciation of the invention and many of the attendant advantages thereof will be readily obtained as the same becomes better understood by reference to the following Figures in conjunction with the detailed description below.

DETAILED DESCRIPTION OF THE INVENTION

Figure 1:
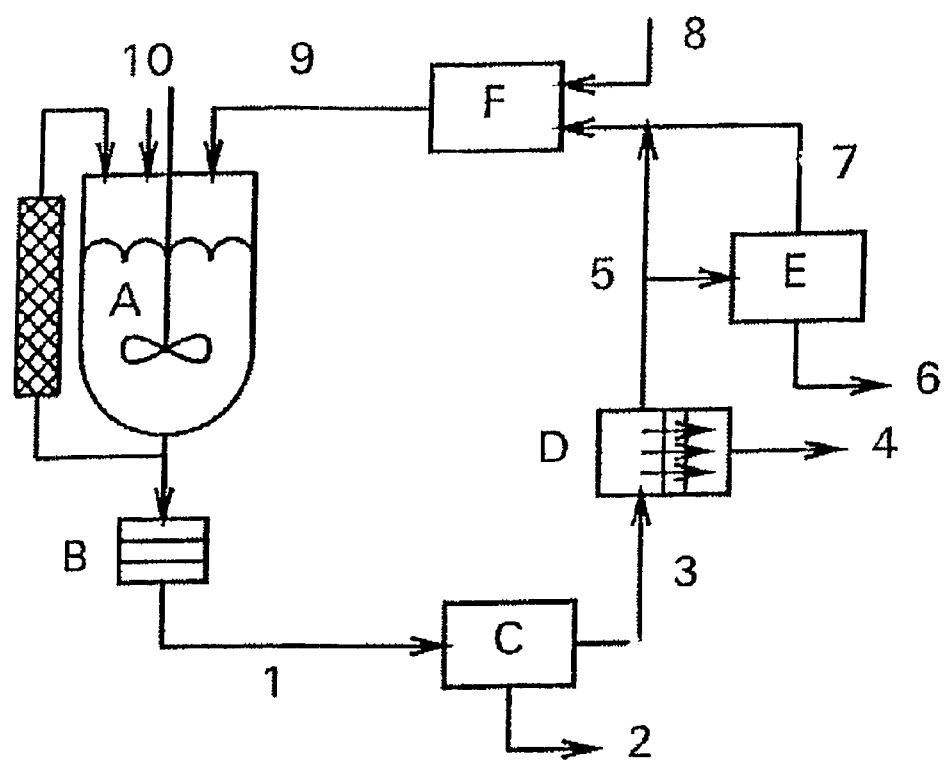
FIG. 1: Flow diagram of a representative process according to the present invention.

The work-up process of the invention is outlined in FIG. 1.

It can be carried out either continuously or batchwise.

The reactor output 1 consists of a solution of a ketone oxime in a polar organic solvent which is partially or completely miscible with water. Solvents used are preferably short-chain alcohols which have 1–6 carbon atoms and are completely or partially miscible with water, for example methanol, ethanol, n-propanol, isopropanol, n-butanol, tert-butanol and amyl alcohol. If a pulverulent catalyst is used for the ammoximation, it can be separated off by means of a filter B. As filter, it is possible to use all known types of filter, for example a pressure filter or a filter centrifuge.

If, as shown in FIG. 1, a circulation reactor with a fixed bed is used, the filter B serves only as a backup to remove solid impurities such as suspended particles or abraded material from the shaped body from the reaction mixture.

The ammoximation of the ketone in the reactor A can be carried out to complete or partial conversion, and the reactor A in the drawing can represent either a single reactor or an assembly of a plurality of reactors connected in series or in parallel.

Ketone conversions of from 30% to 100%, preferably above 50%, are typically achieved in the ammoximation, so that not only the respective oxime but also amounts of unreacted starting material can be present in the reactor output.

The reaction conditions are chosen so that starting material and product are completely in dissolved form in the reactor output (stream 1) under the conditions chosen (temperature, amount of solvent and water content).

Typical conditions for the reactor output in the case of, for example, cyclododecanone oxime are temperatures of 60° C.–90° C. and oxime concentrations of from 5% by weight to 25% by weight, with the reaction advantageously being carried out just below the solubility limit of the oxime in order to limit the amount of solvent. The proportion of water in the reactor output is typically 5% by weight–15% by weight, but can also be higher.

A further advantage of the work-up process of the invention is that ammonium ions as cocatalyst can, if desired, also be present as a homogeneous solution in the reaction mixture 1, as described in DE 101 03 581. Their concentration depends on the solubility of the respective salts in the solvent. If the reaction is carried out in aqueous solutions of short-chain alcohols such as ethanol, the ammonium ion concentration is typically 0.01 mol/l–0.5 mol/l, with suitable ammonium salts being, in particular, those of organic carboxylic acids, for example ammonium acetate.

The key part of the work-up concept of the invention is the crystallizer (crystallization vessel) C in combination with the pervaporation unit/vapor permeation unit D.

In the crystallizer C, the oxime is crystallized in the process of the invention by cooling the reactor output. Optionally, the crystallization can also be completed by addition of further water, but it needs to be noted that this has to be removed again in the further work-up step D.

Figure 2:
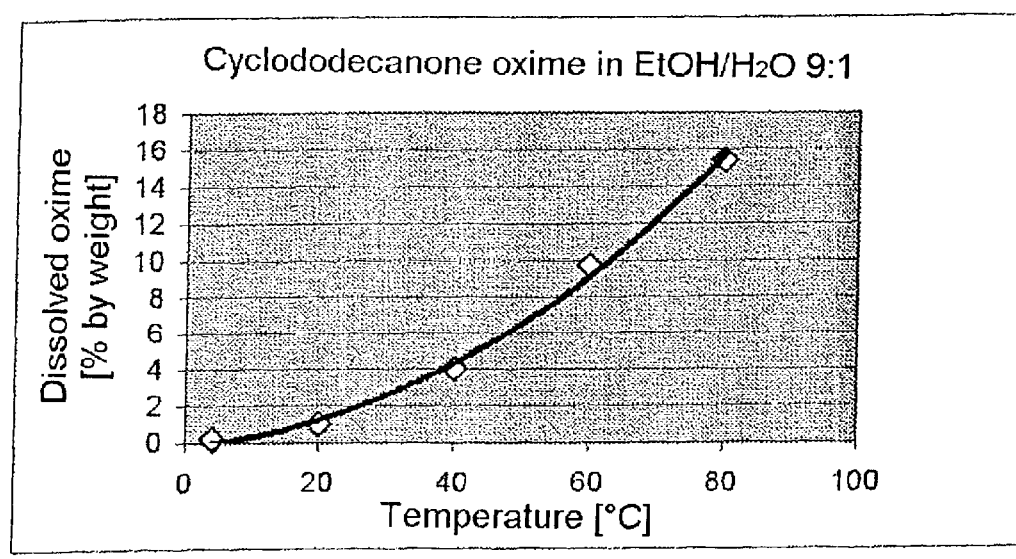
FIG. 2: the solubility of cyclododecanone oxime in a mixture of ethanol and water in a ratio of 9:1 as a function of temperature.

The crystallizer is generally operated at temperatures in the range from −20° C. to +40° C., advantageously from −10° C. to +25° C. Well-suited cooling media are cooling water or refrigerated brine. The lower limit of the temperature window is imposed by the need for no water to freeze out in the crystallizer and for starting material to remain in solution in the case of incomplete conversion. FIG. 2 shows, by way of example, the solubility of cyclododecanone oxime in a mixture of ethanol and water in a ratio of 9:1 as a function of temperature.

The oxime which has crystallized out (stream 2) is separated off as a solid. The crystals which are wet with mother liquor can be washed with a little alcohol/water and dried. Recrystallization is possible in principle, but is generally not necessary. In the case of cyclododecanone oxime, for example, a purity of >99.9% by weight was achieved in the experiments. The proportion of unreacted cyclododecanone in the crystals is generally <0.01% by weight. This is also the case for incomplete conversion in the ammoximation. The crystals (2) can, dissolved in suitable solvents, be used directly for subsequent reactions. A typical subsequent reaction is the Beckmann rearrangement of cyclododecanone oxime to lauryl lactam in concentrated sulfuric acid.

The alcoholic-aqueous mother liquor (3) in the process of the invention still contains from 0.01% by weight to 5% by weight of oxime, preferably from 0.01% by weight to 2% by weight of oxime, and also, depending on the conversion in the ammoximation, amounts of ketone. It also contains residual ammonia and hydrogen peroxide. Furthermore, it can optionally also contain homogeneously dissolved ammonium ions, as described in DE 101 03 581. It is fed via a heat exchanger (not drawn in) directly to pervaporation or vapor permeation. This is typically carried out at from 50° C. to 180° C., advantageously from 80° C. to 140° C., under the respective vapor pressure of the solvent or a slight overpressure.

In pervaporation, the solution 3 is conveyed directly past the membrane, with water diffusing through the membrane. If the solution 3 has a high ketone content as a result of incomplete conversion, the flux through the membrane can be reduced over time due to deposition of the ketone on the membrane. The same phenomenon also occurs when solution 3 contains ammonium ions. An effective remedy here is, surprisingly, a slight modification in the form of vapor permeation.

In the case of vapor permeation, a gas bubble forms over the solution 3. This is compressed or liquefied again in a compressor and conveyed past the membrane, with the water being selectively removed from it. Downstream of the membrane, the stream is depressurized via a flow restrictor, the vapors are heated and passed through the solution 3. This results in further water being vaporized from the solution. Salts and ketone remain in the solution 3. This enables blockage of the membrane to be minimized.

The energetic advantage of the two membrane processes, pervaporation and vapor permeation, is that only the enthalpy of vaporization of the water removed has to be introduced, while in the case of distillation, the enthalpy of vaporization of the total amount of solvent (alcohol) has to be supplied.

The membrane type and its pore diameter is critical for the selectivity. Suitable membranes include both polymer membranes, for example those based on polystyrene, polyacrylate and polysiloxanes, and inorganic membranes, for example those having zeolite or silica structures.

The discharged substream (4) comprises the amount of water which has been introduced in the feed stream (10) comprising aqueous hydrogen peroxide solution and ammonia plus the water of reaction formed in the ammoximation reactor A. If water has been added in the crystallizer C, this too has to be removed again.

In the unit D, the proportion of water is usually reduced from 8% by weight–15% by weight in the inflowing stream (stream 3) to about 5% by weight in stream 5. In this range, the membranes used operate very selectively and display good fluxes across them. However, the water content in the inflowing stream can also be reduced to below 1% by weight and thus brought significantly below the content which is established as azeotrope, for example in a distillation without entrainer.

The amount of alcohol, ammonia or other solvent components which diffuse through the membrane (stream 4) is generally low. Oxime and ketone do not go through the membrane or go through it only in traces. After-treatment of this phase by distillation or other means is generally not necessary.

The phase 5 which has largely been freed of the water of reaction can be admixed with fresh ketone (8) in a mixer F and fed back into the reactor.

In a continuous process using technical-grade feedstocks, by-products which are inactive in the ammoximation can accumulate over time. Thus, for example, technical-grade cyclododecanone usually contains traces of cyclododecane and cyclododecanol. It is therefore advantageous to branch off a substream from 5, either continuously or discontinuously, and to free this of secondary components by distillation. The solvent mixture 7 which has been purified in this way is combined with the main stream 5 in the mixer F and then returned to the ammoximation reactor.

The secondary components are discharged from the process in substream 6.

The process is particularly suitable for the ammoximation of bulky alkanones and cycloalkanones having, in particular, from 8 to 20 carbon atoms, for example cyclooctanone, cyclodecanone, cyclododecanone, cyclopentadecanone and acetophenone.

EXAMPLES

Having generally described this invention, a further understanding can be obtained by reference to certain specific examples which are provided herein for purposes of illustration only and are not intended to be limiting unless otherwise specified.

Example 1
(ammoximation):

In a 1.6 l autoclave, 73 g (400 mmol) of cyclododecanone (CDON) are dissolved in 535 g of about 96% strength ethanol. At 80° C., dry ammonia gas is passed into the reactor and a pressure of 1.6 bar is set (about 14 g of ammonia). The reaction mixture is passed by means of a circulation pump at a flow rate of 600 ml/min over a fixed bed comprising 200 g of shaped catalyst bodies (titanium silicalite TS-1 with 20% by weight of acidic aluminum oxide as described in EP 100 47 435, Degussa AG). Over a reaction time of 4 hours, 40.8 g of a 50% strength by weight aqueous hydrogen peroxide solution (=600 mmol of $H_2O_2$) are metered in. The hydrogen peroxide solution is introduced upstream of the reactor. Gaseous by-products are removed from the reaction mixture via a flow restrictor and further ammonia is introduced in an amount corresponding to that which is lost in this way, about 2 g over a period of 240 minutes. After addition is complete, the reaction mixture is stirred for another 60 minutes. The CDON conversion to the oxime is 95.3% (GC analysis). The proportion of by-products is below 0.1%.

Example 2
(ammoximation):

The procedure of example 1 is repeated, but 5.8 g (0.1 mol/l) of ammonium acetate are additionally dissolved homogeneously in the reaction mixture as described in EP 101 03 581. 523 mmol of $H_2O_2$ are metered in over a period of 180 minutes, and the reaction mixture is subsequently stirred for another 60 minutes. The CDON conversion is >99.9% (GC analysis).

Example 3
(crystallization):

The reaction mixture from example 1 is discharged from the autoclave, unreacted ammonia gas is given off on depressurization and can be condensed by means of a cold trap and returned to the process. The reaction mixture is cooled to 4° C. and the precipitate formed is separated off after 2 hours by means of a filter. The precipitate is washed with a little cold ethanol/water 9:1. Drying at 60° C./200 mbar gives 72.6 g of CDON oxime having a purity of >99.8%.

The mother liquor (about 590 g) comprises aqueous ethanol in which about 3.4 g of CDON and about 2.6 g of oxime are present in dissolved form. Water which has been introduced and water which has been liberated in the ammoximation and also that in the washing solution after the crystallization increases the water content in the ethanolic solution from about 4% by weight to about 11% by weight (about 62 g).

Example 4
(crystallization):

The reaction mixture from example 2 is worked up by a method similar to example 3. This gives 76.4 g of CDON oxime having a purity of >99.8%. The mother liquor (about 580 g) comprises aqueous ethanol in which about 2.5 g of oxime and <0.1 g of CDON are present in dissolved form. The water content is about 10% by weight (about 58 g). 5.8 g of ammonium acetate are present in dissolved form in the mother liquor.

Example 5
(pervaporation):

A sample of the mother liquor from example 3 is conveyed at 90° C. past a Sulzer Chemtech 2201 polymer membrane until the water content in the solution has been reduced to about 4%. The water content of the permeate is above 98%, and the flux drops during the experiment from 0.5 kg/m²*h to 0.2 kg/m²*h as the water content of the feed decreases.

Example 6
(pervaporation):

A sample of the mother liquor from example 3 is conveyed at 120° C. in a manner analogous to example 5 past an NaA zeolite membrane (from Mitsui). The water content of the permeate is 96% and drops to 94% by the end of the experiment. The flux drops during the experiment from 3.5 kg/m²*h to 2.6 kg/m²*h as the water content of the feed decreases.

Example 7
(pervaporation):

The experiment of example 6 is repeated at 80° C. using an NaY membrane (from Mitsui). The water content of the permeate is 78% and drops to 68% by the end of the experiment. The flux drops during the experiment from 2.8 kg/m²*h to 1.7 kg/m²*h as the water content of the feed decreases.

Example 8
(pervaporation)

The experiment of example 6 is repeated at 140° C. using an inorganic silica membrane (Sulzer Chemtech SMS). The water content of the permeate is 88% and drops to 70% by the end of the experiment. The flux drops from 10.1 kg/($M^{2*}h$) to 5.0 kg/($m^{2*}h$) as the water content of the feed decreases.

Example 9
(vapor permeation):

A sample containing ammonium acetate from example 4 is partly vaporized, the vapor is passed through a droplet precipitator, compressed and conveyed past an inorganic silica membrane (Sulzer Chemtech SMS). The water content of the permeate is 90%–92%, and the flux is 0.8 kg/m²*h.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 42 620.8, filed on Aug. 31, 2001, and incorporated herein by reference.

What is claimed is:

1. A process for the work-up of a reaction mixture containing an oxime formed by ammoximation of a ketone with hydrogen peroxide and ammonia in a homogeneous solution containing a solvent over a titanium-containing catalyst, comprising the steps of:

removing the catalyst, separating the oxime from the reaction mixture, removing water of reaction from the reaction mixture, and recirculating the solvent, wherein at least one of said steps comprises a membrane separation.

2. The process of claim 1, wherein the solvent is a polar, organic liquid which is substantially or completely miscible with water.

3. The process of claim 1, wherein the solvent is a short-chain alcohol.

4. The process of claim 3, wherein the solvent is a short-chain alcohol selected from the group consisting of methanol, ethanol, n-propanol, isopropanol, n-butanol, tert-butanol, and amyl alcohol.

5. The process of claim 1, wherein the water of reaction is removed from the reaction mixture using the membrane.

6. The process of claim 1, wherein the oxime is selectively separated off from the process by crystallization and the water of reaction is separated off from the mother liquor by pervaporation using the membrane.

7. The process of claim 1, wherein the oxime is firstly separated off from the process by crystallization and the water of reaction is separated off from the mother liquor by vapor permeation using the membrane.

8. The process of claim 1, wherein the solvent is a polar organic solvent, and the polar solvent from the mother liquor is returned to the ammoximation reaction.

9. The process of claim 1, wherein the membrane is a polymer membrane.

10. The process of claim 9, wherein the polymer membrane is selected from the group consisting of polystyrene, polyacrylates, and polysiloxanes.

11. The process of claim 1, wherein the membrane comprises at least one inorganic material.

12. The process of claim 11, wherein the membrane has a zeolite or silica structure.

13. The process of claim 1, wherein the oxime is separated from the reaction mixture in a crystallizer and wherein the crystallizer is operated at temperatures in the range from −20° C. to +40° C.

14. The process of claim 6, wherein the pervaporation is carried out at from 50° C. to 180° C.

15. The process of claim 6, wherein the pervaporation is carried out at from 80° C. to 140° C.

16. The process of claim 7, wherein the vapor permeation is carried out at from 50° C. to 180° C.

17. The process of claim 7, wherein the vapor permeation is carried out at from 80° C. to 140° C.

18. The process of claim 1, wherein the ketone is selected from the group consisting of cyclooctanone, cyclodecanone, cyclododecanone, cyclopentadecanone, and acetophenone.

19. The process of claim 1, wherein the ketone has 8 to 20 carbon atoms.

20. The process of claim 1, further comprising subjecting the oxime separated from the reaction mixture to a Beckmann rearrangement.

* * * * *